United States Patent [19]

Herdle

[11] Patent Number: 4,888,425
[45] Date of Patent: Dec. 19, 1989

[54] PREPARATION OF POLYALKYLENE POLYAMINES

[75] Inventor: William B. Herdle, Greenburgh, N.Y.

[73] Assignee: Union Carbide Chemicals and Plastics Company Inc., Danbury, Conn.

[21] Appl. No.: 576,807

[22] Filed: Feb. 7, 1984

Related U.S. Application Data

[63] Continuation of Ser. No. 373,726, Apr. 30, 1982.

[51] Int. Cl.$^4$ .......................................... C07D 295/12
[52] U.S. Cl. ................................... 544/402; 544/357; 564/479; 564/480; 564/512
[58] Field of Search ................................ 564/479–480, 564/512; 544/402, 357; 260/939, 959

[56] References Cited

U.S. PATENT DOCUMENTS

| | | | |
|---|---|---|---|
| 3,121,115 | 2/1964 | Meuly | 544/42 |
| 4,036,881 | 2/1977 | Brennan et al. | 564/479 |
| 4,044,053 | 8/1977 | Brennan et al. | 564/479 |
| 4,316,840 | 2/1982 | Ford et al. | 564/512 |
| 4,316,841 | 2/1982 | Ford et al. | 544/402 |
| 4,324,914 | 4/1982 | McConnell | 564/479 |
| 4,552,961 | 11/1985 | Herdle | 544/402 |

*Primary Examiner*—Donald G. Daus
*Attorney, Agent, or Firm*—Gerald L. Coon

[57] ABSTRACT

Enhanced production of predominantly linearly extended polyalkylene polyamines from alkylenediamines reacted with alkylene glycols or alkanolamines using a phosphorus-containing catalyst is achieved by removing water during the reaction.

19 Claims, No Drawings

PREPARATION OF POLYALKYLENE POLYAMINES

This application is a continuation of application Ser. No. 373,726, filed Apr. 30, 1982.

BACKGROUND OF THE INVENTION

1. Field of the Invention

This invention relates to the production of polyalkylene polyamines, and more particularly to a process for enhancing the production of predominantly linearly extended polyalkylene polyamines while substantially avoiding the production of heterocyclic by-products.

2. Description of the Prior Art

Several patents, including, for example U.S. Pat. Nos. 4,036,881 (Brennan I) and 3,044,053 (Brennan II), disclose the preparation of predominantly non-cyclic polyalkylene polyamines from the condensation of an alkanolamine or alkylene glycol compound with an alkylenediamine compound. These patents, however, disclose that it is not critical to control the amount of water present during the heating of reactants and catalyst. For example, Brennan I discloses from column 5, line 65 to column 6, line 3 that "it is not critical to control the amount of water of reaction present during the heating of reactants and catalyst, such as by removal thereof as it is formed. Usually, we prefer to retain water in the reaction zone and remove it from the reaction mass during recovery of the predominantly non-cyclic polyalkylene polyamines." It is therefore disclosed that a preferred embodiment of the Brennan process is to retain water in the reaction zone and remove it from the reaction mass during recovery of the product. In addition, the disclosed process even provides for the addition of water to the reaction mass to generate an aqueous solution for conducting the process, such as described in Example II in Brennan I.

It has been discovered, in direct contradiction to these disclosures, that not only is water removal desirable during the production of predominantly non-cyclic polyalkylene polyamines using a phosphorus catalyst, but that water removal provides for enhanced conversion rates of the reactants.

Although not wishing to be bound to any particular theory, a basis for this discovery of increased conversion rates when water is removed from the reaction zone may be as follows. A schematic representation for the process of the present invention, as well as the process in the Brennan patents, is presented in Formula I below:

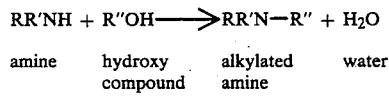

amine  hydroxy  alkylated  water
       compound  amine

This overall equation is irreversible in that the alkylated amine product does not readily react with water to generate an amine and a hydroxy compound. For this reason, it cannot be predicted from this overall equation that the presence of water would be a contributing factor in reaction efficiency. Instead, it was well established in the prior art, through the Brennan patents, that water was not a critical component in the overall process.

It is believed, however, that an intermediate step not appreciated by the prior art, identified by Formula III below, is responsible for establishing the criticality of the presence of water during the reaction. According to the theory a reversible reaction exists, as an intermediate step to the formulation of polyalkylene polyamines, in which the phosphorus catalyst or acid intermediate condenses with the hydroxy reactant to form a phosphorus ester as shown in Formula II:

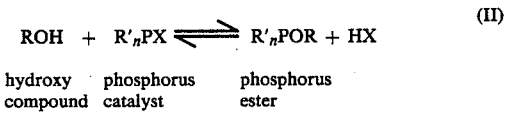

hydroxy    phosphorus    phosphorus
compound   catalyst      ester in which X is a radical as hereinafter defined including hydroxyl, amide, or halo groups. The phosphorus ester may subsequently enter into a similar equilibrium with water according to Formula III:

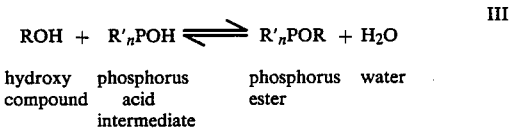

hydroxy    phosphorus   phosphorus  water
compound   acid         ester
           intermediate Obviously when X is a hydroxyl group, Formula II merges with Formula III for phosphorus acid catalysts. Since this reaction is reversible, removal of water, added previously or formed during the reaction, shifts the equilibrium towards the formation of the phosphorus ester. The increased concentration of this ester is believed to be responsible for providing increased conversion rates to linearly extended polyalkylene polyamines.

Water removal has been disclosed in various amine production processes. For example, U.S. Pat. No. 3,121,115 (Meuly) contains a disclosure for the production of aminoalkylated compounds containing tertiary amino groups. The disclosed process involves reacting alkylatable amines or phenols with N-tertiary aminoalkanols in the presence of a phosphoric acid catalyst. There is no disclosure of an alkylenediamine reactant, since the patent is limited to specifically describing monoamines or aromatic diamines. There is also no disclosure of a difunctional alkylene glycol or alkanolamine reactant, since the patent is specifically limited to monofunctional, tertiary aminoalkanol reactants. As a consequence, there is no production of predominantly linearly extended polyalkylene polyamines, nor is there any appreciation for the formation of cyclic compounds, since the patent does not relate to polycondensation reactions upon which the formation of cyclic compounds is based. Similarly, U.S. Pat. No. 4,103,087 (Brennan III) presents an improved process for reacting tertiary aminoalkanols with monofunctional secondary amines to produce a di-(N,N-disubstituted amino)alkane product. Both patents are distinguishable from the process of the present invention since their disclosures of water removal for amine condensation reactions in general does not present evidence to contradict the specific teaching in the Brennan patents that polyalkylene polyamine condensation reactions are not dependent upon water concentration. There is no indication or suggestion in the Brennan III or Meuly patents that intermediate reactions in the production of polyalkylene polyamines involving difunctional alkylene glycol or alkanolamine compounds would be reversible, thereby establishing a dependency upon water concentration.

Water removal has also been disclosed in other amine production processes, such as in U.S. Pat. Nos. 4,210,605 (Hoshino et al) and 4,254,060 (Kimura et al) in order to avoid the deactivation of particular homogeneous, metal containing, colloidal catalysts. These patents do not relate to condensation reactions involved in the production of polyalkylene polyamines, such that there is no appreciation that specific intermediate steps may be dependent upon water condensation.

U.S. Pat. No. 3,714,259 (Lichtenwalter et al) discloses an alternative process for the production of linear polyalkylene polyamines using a hydrogenation catalyst. There is no disclosure of water removal, or that the use of a phosphorus-containing catalyst would create a dependency on water concentration.

SUMMARY OF THE INVENTION

The present invention relates to a process for producing predominantly linearly extended polyalkylene polyamines comprising:

(a) contacting (i) an alkylenediamine with (ii) a difunctional hydroxy alkylene compound selected from the group consisting of alkylene glycols and alkanolamines; (iii) in the presence of a catalytically effective amount of a phosphorus acid or acid derivative compound; (b) removing water, preferably continuously, during the reaction; and (c) recovering the polyalkylene polyamines. This reaction is usually conducted at temperatures of above about 250° C. to about 350° C., and at a pressure sufficient to provide a reaction mixture in a liquid phase, usually from about 200–2500 psig; and for a time period sufficient to provide a total reaction conversion of from about 10% to about 80%, usually occurring within from 10 minutes to 20 hours.

The alkylenediamine includes cyclic or non-cyclic alxyleneamine compounds having the structure:

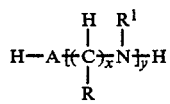
(III)

wherein A is

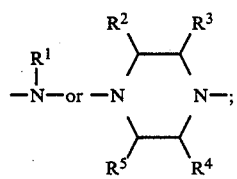

x is an integer greater than 1, preferably from 2 to about 6; y is an integer from 0 to about 6, preferably from 0 to about 2; wherein when y is 0, A is

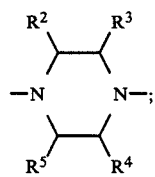

and each R, $R^1$, $R^2$, $R^3$, $R^4$ and $R^5$ is a hydrogen or lower alkyl, preferably hydrogen.

The difunctional hydroxy alkylene compound includes cyclic or non-cyclic compounds with the structure:

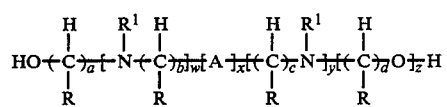
(IV)

wherein A is

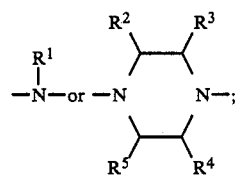

each R, $R^1$, $R^2$, $R^3$, $R^4$, and $R^5$ is hydrogen or lower alkyl, preferably hydrogen; each a, b and c is any integer greater than 1, preferably 2 to about 6; d is 0 or an integer greater than 1; each x and z is 0 or 1; each w and y is any integer from 0 to about 6, preferably from 0 to about 2; provided that d, w and y are 0 and z is 1 when x is 0; and z is 0 when x is 1 and d is 0.

DETAILED DESCRIPTION OF THE INVENTION

The present invention provides for an improved process for producing predominantly linearly extended polyalkylene polyamines in enhanced conversion rates by reacting an alkylenediamine with an alkylene glycol or alkanolamine, in the presence of a phosphorus-containing catalyst, wherein water is removed during the reaction.

Reactants

The alkylenediamine reactants are defined as cyclic or non-cyclic compounds, or mixtures of compounds, which contain two primary or secondary, preferably primary, amines separated by alkylene chains. The alkylenediamines that can be generally employed in the present invention include those having the structure:

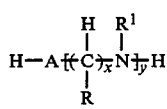
(III)

wherein A is

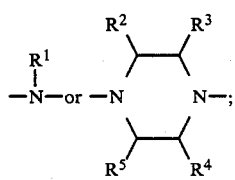

x is an integer greater than 1, preferably from 2 to about 6; y is an integer from 0 to about 6, preferably from 0 to about 2, wherein when y is 0 A is

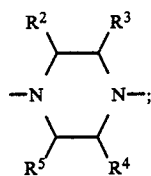

R, $R^1$, $R^2$, $R^3$, $R^4$ and $R^5$ are hydrogen or lower alkyl, preferably hydrogen.

Some examples of alkylenediamines that can be used as reactants in the process of the present invention, along with their structure defined by the parameters in Formula III, include those listed in Table 1:

TABLE 1

| REPRESENTATIVE ALKYLENEDIAMINE REACTANTS | | | | | |
|---|---|---|---|---|---|
| Alkylenediamine | A | x | y | R | $R^1$ |
| Piperazine | peperazino | — | 0 | — | — |
| N—(2-aminoethyl)-piperazine | " | 2 | 1 | both H | H |
| N—(2-(2-aminoethylamino)-ethyl)-piperazine | " | 2 | 2 | all H | all H |
| Ethylenediamine | amino | 2 | 1 | both H | both H |
| 1,3-Propanediamine | " | 3 | 1 | all H | both H |
| Hexamethylenediamine | " | 6 | 1 | all H | both H |
| Diethylenetriamine | " | 2 | 2 | all H | all H |
| Linear triethylenetetramine | " | 2 | 3 | all H | all H |
| Linear tetraethylenepentamine | " | 2 | 4 | all H | all H |
| N,N'—dimethyl-ethylenediamine | " | 2 | 1 | both H | both $CH_3$ |
| 1,2-Propanediamine | " | 2 | 1 | $CH_3$,H | both H |

Particularly preferred alkylenediamine reagents include ethylenediamine and piperazine. Piperazine is a preferred cyclic reactant for the reason that the process of the present invention provides for the relatively selective attachment of non-cyclic alkyleneamine groups onto the piperazine cyclic ring. In this manner, the cyclic by-products formed during the production of polyalkylene polyamines may be given greater utility by increasing the linear structures within the molecules.

The difunctional hydroxy alkylene reactants are defined as cyclic or non-cyclic compounds, or mixtures of compounds, containing a difunctional alkylene moiety connected at one point to a hydroxy group and at another point, either directly or through a chain of one or more alkyleneamine groups, to another hydroxy group or to an amino group that has at least one hydrogen substituent. The term therefore comprises the classes of alkylene glycols and alkanolamines having active amine hydrogens. Such compounds include those with the structure:

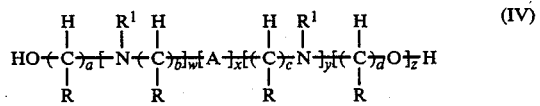  (IV)

wherein A is

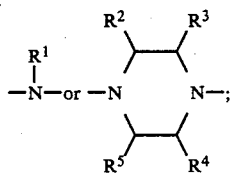

each R, $R^1$, $R^2$, $R^3$, $R^4$, and $R^5$ is hydrogen or lower alkyl, preferably hydrogen; each a, b and c is any integer greater than 1, preferably 2 to about 6; d is 0 or an integer greater than 1; each x and z is 0 or 1; each w and y is any integer from 0 to about 6, preferably from 0 to about 2; provided that d, w and y are 0 and z is 1 when x is 0; and z is 0 when x is 1 and d is 0.

The alkylene glycol reactants include the noncyclic diols of lower alkylene groups. Examples of alkylene glycol compounds are ethylene glycol, propylene glycol, butylene glycol, trimethylene glycol, hexamethylene glycol, and the like. A preferred alkylene glycol is ethylene glycol.

The alkanolamine reactants include such compounds as monoethanolamine, diethanolamine, N-(2-aminoethyl)ethanolamine, propanolamines, N,N-bis(hydroxyethyl)piperazine and the like. Preferred alkanolamines include monoethanolamine and diethanolamine.

The R term in the

groups can, of course, represent either hydrogen or various alkyl groups alternatively within the same alkylene chain of x carbon atoms. Similarly, the $R^1$ term in the

groups can, of course, vary between groups.

The relative proportions of alkylenediamine to difunctional hydroxy alkylene compound utilized can be from about 6:1 to about 1:1, preferably about 3:1 to about 1:1, based on the molar equivalents of alkylenediamine compound to hydroxy groups. As such, the molar amount of alkylene glycol will usually be about half the molar amount of alkanolamine, used with a given amount of alkylenediamine reactant.

Particularly preferred embodiments of the invention include condensation reactions of etnylenediamine with either monoethanolamine or ethylene glycol.

Catalyst

The catalyst utilized in the process of the present invention is a phosphorus acid or acid derivative compound. The term phosphorus acid or acid derivative defines compounds having a P-X bond wherein P is a phosphorus atom bonded to a halogen, oxygen, sulfur or nitrogen atom in X which is a radical capable of 1)

hydrolyzing to produce the corresponding phosphorus acid structure, or 2) exchanging with a hydroxyl group from the hydroxy alkylene reactant to provide a phosphorus ester.

The phosphorus acid or acid derivative catalyst in the present invention is believed to function by forming with the alkanolamine or alkylene glycol compound a phosphorus ester in situ. For this reason, it is believed that a requirement for a good phosphorus catalyst is that it contain as a substructure an atom bonded to phosphorus that can be replaced readily by the oxygen atom of a hydroxyl group of the difunctional hydroxy alkylene compound. Such a replaceable atom might be oxygen (as in the case of phosphorous or phosphoric acids or their esters), halogen, nitrogen (as in the case of amides of phosphorous or phosphoric acids) or another atom that can be transformed into a phosphorus ester by a similar process.

Phosphorus-containing compounds such as trialkyl and triaryl phosphines and phosphine oxides, which contain no such exchangeable substructure, do not function as catalysts in the subject process. Very sterically hindered phosphorus compounds such as hexaethyl phosphoric triamide, while containing the requisite exchangeable substructure and functioning to some extent as catalysts for the subject invention, are less preferred catalysts because they undergo the exchange process with the alkanolamine or alkylene glycol hydroxyl moieties only slowly.

Phosphorus acids are defined by those structures wherein X in the P-X radical is a hydroxyl radical. Acid derivatives are defined by structures wherein X is a substitute functional group. Various acids derivatives include: salts when —X is —O$^-$ M$^+$ is a mono or polyvalent cation; amides when —X is bonded to the phosphorus atom through a nitrogen atom; anhydrides when —X contains a second phosphorus atom bonded to the first phosphorus atom through an oxygen atom; esters when —X is —OR; and so on with regard to other functional groups defined by —X. The precise phosphorus acid or acid derivative structure is not critical so long as it fulfills the following two functional requirements: (1) that it provides for the relatively selective production of predominantly linearly extended polyalkylene polyamines and (2) that it enables increased conversion rates for polyalkylene polyamine production when water is removed during the reaction, possibly due to the water-inhibited formation of a phosphorus intermediate compound during the reaction.

The phosphorus acids or acid derivative catalysts include those having the structure:

(V)

wherein Y is an oxygen or sulfur atom; n is 0 or 1; X is hydroxy, alkoxy, aryloxy, or the thioanalogs of the foregoing, alkyl or aryl substituted amino, halo, or the salts or phosphorus anhydrides or thioanhydrides of the foregoing when X is hydroxy or mercapto; R' and R" are hydrogen, alkyl, aryl or one of the groups previously defined by X.

Suitable phosphorus acid or acid derivatives which can be employed include, for example, acidic metal or semi-metal phosphates, phosphoric acid compounds, and their anhydrides, phosphorous acid compounds and anhydrides, alkyl or aryl phosphates, alkyl or aryl phosphites, alkyl or aryl substituted phosphonic acids and phosphinic acids, alkali metal monosalts of phosphoric acid, phosphorous amides and phosphoric amides, the thioanalogs of the foregoing, and mixtures of any of the above.

Suitable acidic metal or semi-metal phosphates include boron phosphate, ferric phosphate, aluminum phosphate and the like.

Suitable phosphoric acid compounds include aqueous or anhydrous phosphoric acids, such as orthophosphoric acid, pyrophosphoric acid, metaphosphoric acid, and condensed phosphoric acids such as polyphosphoric acids.

Any commercially available mono-, di-, or trialkyl or aryl phosphate or phosphate ester can be employed. In addition, bis-(phosphates) and secondary phosphate esters, such as those disclosed in U.S. Pat. Nos. 3,869,526 (Combey et al) and 3,869,527 (Hogberg et al), respectively, can be utilized.

Suitable alkyl or aryl substituted phosphonic acids or phosphinic acids include alkyl phosphonic acids, aryl phosphonic acids, alkyl phosphinic acids and aryl phosphinic acids.

Examples of such phosphorus acid or acid derivative compounds include phenylphosphinic, ethylphosphonic, phenylphosphonic, naphthaphosphonic, and methylphosphinic acids; methyl phenylphosphonate, dimethyl phenylphosphonate, methyl phenylphosphinate, ethyl naphthaphosphinate, propyl methylphosphonate; hexamethyl phosphoric triamide, hexaethyl phosphoric triamide and their analogous phosphorous triamides.

Preferred phosphorus catalysts include hexamethyl phosphorous triamide, hexaethyl phosphorous triamide, boron phosphate, ferric phosphate, aluminum phosphate, phosphoric acid and phosphorous acid.

The amount of phosphorus acid or acid derivative catalyst utilized is a catalytically effective amount to cause condensation of the reactants to produce predominantly linearly extended polyalkylene polyamines. This quantity will vary depending upon the reaction conditions and catalyst utilized. Usually a catalytically effective amount will be from about 0.01 to about 10 mole percent, and preferably from about 1 to about 3 mole percent, based on the moles of hydroxy alkylene compound used.

Catalyst may be charged to the reaction in the form of aqueous solutions; however, the water so charged should be removed before or during the reaction.

Reaction Adjuvants and Conditions

The reaction is generally conducted at temperatures of from above about 250° to about 350° C., preferably from about 280° to about 310° C., and most preferably at around 300° C. The reaction is conducted at a pressure sufficient to provide a reaction mixture in a liquid phase, preferably at a pressure of about 200 to about 2500 psig, and most preferably at a pressure of from about 300 to about 700 psig. The reaction is typically conducted for a time period sufficient to provide a total reaction conversion of from about 10% to about 80%, generally within from about ten minutes to twenty hours.

It is preferred that the reaction be conducted without the presence of a solvent; however, the reaction could be conducted using an organic solvent which does not exhibit a deleterious effect upon the reaction.

The process of the present invention may be carried out batchwise or continuously by employing conventional process techniques and apparatus well known to those skilled in the art. In continuous reaction processes, the phosphorus catalyst may be added alone or in combination with the reactants. Alternatively, the catalyst may be provided as a fixed bed on conventional support materials well known to those skilled in the art.

Water Removal

It has been discovered that it is desirable to limit the amount of water present during the reaction to increase reaction conversion rates. The amount of water can be reduced by removal of any residual water in the reaction mixture, and by removal of the water of reaction as it is formed. It is preferred that the water be removed continuously during the reaction process. The procedure for removing water continuously during the reaction can be any of the well established procedures in the art. In a preferred embodiment, water is removed by drawing off a portion of a gaseous phase of water and reaction mixture as by distillation.

Once a water-containing mixture is withdrawn from the reaction zone, by whatever means, water can be separated from the mixture so withdrawn by procedures well established in the art, such as those described in U.S. Pat. No. 4,032,411 (Tornquist et al). The relatively anhydrous mixture so produced can be recycled to the reaction.

Procedures that can be utilized for separating water from the withdrawn reaction mixture include fractional or azeotropic distillation, adsorption using for example molecular sieves, absorption, and the like. The amount of water withdrawn from the reaction is preferably such as to minimize the water retained during the reaction process.

Product

The predominantly linearly extended polyalkylene polyamine product may be recovered using conventional procedures, well established in the art, such as distillation or filtration. The polyalkylene polyamine produced by the process of the present invention is predominantly linearly extended in the sense that the phosphorus acid or acid derivative catalyst provides for the selective formation of linear alkylene chains through polycondensation reactions, minimizing the production of cyclic by-products. When using cyclic reactants containing piperazine substructures, a polyalkylene polyamine product is selectively produced which contains these piperazine groups extended or connected by predominantly linear alkyleneamine groups with mininal formation of additional cyclic substructures.

The process of the present invention for reacting alkylenediamines, i.e., compounds containing at least two amine groups containing active hydrogen atoms, with difunctional hydroxy alkylene compounds, i.e., difunctional hydroxy compounds capable of condensing with active hydrogen atoms, provides for a complex series of polycondensation reactions to occur generating a variety of polyalkylene polyamine products.

The preferred predominantly linearly extended polyalkylene polyamines have the structure:

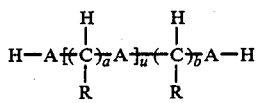

wherein R and A are as previously defined; each a and b is any integer greater than 1, preferably from 2 to about 6; and u is an integer from 1 to about 6. Representative examples of such compounds include:

diethylenetriamine from ethylenediamine and monoethanolamine;

linear triethylenetetramine from ethylene glycol and etnylenediamine;

N-(2-aminoethyl)piperazine and N,N'-bis(2aminoetnyl)piperazine from piperazine and monoethanolamine;

N,N'-bis(2-aminoethyl)piperazine and N-(2-(2-aminoethylamino)ethyl)-piperazine from N-(2-aminoethyl)-piperazine and monoethanolamine;

linear tetraethylenepentamine from ethylenediamine and dietnanolamine; and linear triethylenetetramine from ethylenediamine and N-(2-hydroxyethyl)ethylenediamine.

Most preferred compounds are dietnylenetriamine, linear tetraethylenepentamines and triethylenetetramines.

In a typical embodiment of the invention, the alkylenediamine is mixed with the difunctional hydroxy alkylene compound and heated in the presence of the phosphorus acid or acid derivative compound at a temperature of from above about 250° to about 350° C., at a pressure sufficient to provide a reaction mixture in a liquid phase, which is usually from about 200 to about 2500 psig. The reaction is conducted in a vessel in which the vapor pressure of the reaction mixture generates a gaseous phase of water and reaction mixture during the reaction. A portion of this gaseous phase is removed, preferably continuously, from the reaction vessel. Water is separated from the mixture so removed and the remaining relatively anhydrous reaction mixture is recycled to the reaction. The predominantly linearly extended polyalkylene polyamine can be withdrawn at the end of the batch operation once the desired amount of conversion has been achieved. Alternatively, the reactants may be added continuously to a reaction vessel with the polyalkylene polyamine product separated from a reaction mixture which is continuously withdrawn from the reaction vessel.

The analysis of the polyalkylene polyamines produced by the process of the present invention can be conducted by using standard gas chromatography techniques using columns selected for their ability to separate the individual components that may be present in a particular reaction mixture.

The predominantly linearly extended polyalkylene polyamines are useful in a wide variety of applications, such as chemical intermediates in such areas as the manufacture of chelating agents, fuel additives, corrosion inhibitors, paper wet strength resins, polyamide production, ion exchange resins, epoxy curing agents, asphalt additives, urethane catalysts and pharmaceutical applications.

EXAMPLES

The chemical designations used in the Examples are defined as follows:

| Designation | Description |
|---|---|
| AEEA | N—(2-aminoethyl)ethanolamine |
| AEP | N—(2-aminoethyl)piperazine |
| DETA | Diethylenetriamine |
| DRYING AGENT I | 3A Molecular Sieve |
| EDA | Ethylenediamine |
| L-TETA | Linear triethylenetetramine |
| MEA | Monoethanolamine |
| PIP | Piperazine |
| TEPA | Tetraethylenepentamines (all isomers) |
| TETA | Triethylenetetramines (all isomers) |

EXAMPLES 1-10

Examples 1 through 10 were conducted to determine the effect water addition has on the polyalkylene polyamine production process for various catalysts. The experiments were conducted using 3 cm³ tube reactors heated using a fluidized sand bath. The basic procedure was as follows. The tube reactor was charged with about 2 g of a 1:1 molar mixture of EDA and MEA along with the indicated amounts of catalyst and water. The tube was sealed and heated to 300° C., usually in just under 5 minutes, and held at the reaction temperature for about 2 hours. The reaction was then quenched by plunging the tube in water, cooling the reaction to room temperature in about 2 to 3 minutes. The reaction mixture so produced was analyzed using standard gas chromatography with an internal standard.

Examples 1 and 2 were conducted using boron phosphate, $BPO_4$, catalyst. In Example 1 there was no water addition, whereas in Example 2, 0.25 mole per mole MEA of water was added to the reaction. Examples 3 to 6 were conducted using phosphorus acid, $H_3PO_3$, as catalyst. Example 3 was conducted without water addition whereas examples 4, 5 and 6 were conducted using increasing amounts of water added to the reaction. Examples 7-10 were conducted using hexaethylphosphorus triamide, $(Et_2N)_3P$, as catalyst. Example 7 was conducted without water addition, whereas Examples 8, 9, and 10 were conducted with increasing amounts of water added. The results are shown in Table 2 below:

added water. This is entirely unexpected in view of the Brennan I disclosure with examples providing for water addition.

EXAMPLES 11-16

Examples 11 through 16 were conducted to compare the water removal process of the present invention with the general procedure set forth in the prior art wherein water is retained during the reaction and removed during recovery of the predominantly linearly extended polyalkylene polyamine products. The reactions were conducted in a 1-liter stainless steel autoclave with an electric heating jacket and magnetically coupled stirrer. A gas flow line from the reactor vessel was connected to a water-cooled condenser and a drying reservoir containing DRYING AGENT I. A liquid flow line positioned at the downstream end of the drying reservoir passed through a pump and back to the reactor vessel. To prepare for the reactions, the reactor and drying reservoir were charged with the necessary reactants and the autoclave was purged using argon, and heated to the desired reaction temperature of approximately 300° C. The reactor was left open to atmospheric pressure until the internal temperature reached 130° C., and the reactor was then sealed until the final temperature was achieved. Recirculation of reactants was begun by starting the pump such that a mixture of reactants and water vapor in a gaseous phase was continuously removed from the reaction vessel and passed through the drying reservoir. Water was removed in the drying reservoir, and the remaining relatively anhydrous mixture was recycled to the reactor vessel. After the designated reaction time, the pump was stopped, and water was passed through an internal coil to quench the reaction. The internal temperature dropped to below 200° C. within three minutes or less. When the internal pressure fell below atmospheric, the reactor was flooded with argon at atmospheric pressure, then cooled under argon overnight before it was opened and the products removed for standard gas chromatography analysis.

Examples 11 through 14 were conducted using $H_3PO_3$ catalyst, whereas Examples 15 and 16 were

TABLE 2

| | | | SEALED-TUBE REACTIONS WITH ADDED WATER[1] | | | | | | | | |
|---|---|---|---|---|---|---|---|---|---|---|---|
| | Catalyst | | Product Analysis[3] | | | | | | | | MEA |
| Example | Catalyst | Loading[2] | $H_2O$[2] | EDA | MEA | PIP | DETA | AEP | AEEA | TETA | TEPA | Conversion[4] |
| 1 | $BPO_4$ | .0050 | 0.0 | 42.3 | 40.0 | 0.44 | 9.2 | 0.25 | 4.0 | 2.0 | 0.1 | 20.3 |
| 2 | $BPO_4$ | .0056 | 0.250 | 45.5 | 42.6 | ND | 5.7 | 0.10 | 1.6 | 0.8 | 0.1 | 11.7 |
| 3 | $H_3PO_3$ | .0279 | 0.0 | 29.3 | 19.1 | 1.90 | 18.6 | 1.66 | 3.0 | 8.5 | 7.9 | 61.4 |
| 4 | $H_3PO_3$ | .0291 | 0.219 | 30.2 | 22.0 | 1.50 | 16.6 | 1.48 | 3.9 | 8.2 | 7.4 | 54.1 |
| 5 | $H_3PO_3$ | .0289 | 0.584 | 31.5 | 22.6 | 0.92 | 13.0 | 1.10 | 2.7 | 5.2 | 2.1 | 50.3 |
| 6 | $H_3PO_3$ | .0277 | 0.613 | 25.8 | 26.1 | 1.47 | 11.1 | 0.86 | 3.2 | 4.3 | 2.4 | 41.9 |
| 7 | $(Et_2N)_3P$ | .0270 | 0.0 | 27.1 | 16.9 | 2.02 | 16.9 | 1.72 | 1.9 | 9.6 | 9.5 | 64.6 |
| 8 | $(Et_2N)_3P$ | .0266 | 0.111 | 28.5 | 17.9 | 1.85 | 17.6 | 1.59 | 2.7 | 9.4 | 8.7 | 62.1 |
| 9 | $(Et_2N)_3P$ | .0283 | 0.131 | 27.9 | 19.2 | 1.84 | 16.5 | 1.51 | 2.7 | 8.5 | 8.2 | 59.0 |
| 10 | $(Et_2N)_3P$ | .0280 | 0.692 | 33.0 | 30.4 | 0.85 | 9.9 | 0.51 | 2.8 | 3.0 | 0.71 | 30.8 |

Notes:
[1]All reactions run using an EDA/MEA mole ratio of about 1.00, at 300° C. for about 2.0 hours.
[2]Moles per mole MEA.
[3]Weight percent of isolated products by gas chromatography; ND = not detected.
[4]Percent of charged MEA consumed, based on assumed 100% mass balance.

The data presented, for all catalysts, show that the MEA conversion is significantly reduced, indicating a loss in reaction efficiency, due to the presence of the conducted using $BPO_4$ catalyst. The reaction conditions are set forth in Table 3 below:

TABLE 3

COMPARATIVE WATER REMOVAL EXPERIMENTS

| Example | 11 | 12 | 13 | 14 | 15 | 16 |
|---|---|---|---|---|---|---|
| Reactor Charge (g): | | | | | | |
| EDA | 198.0 | 198.0 | 197.1 | 197.2 | 199.34 | 199.30 |
| MEA | 100.6 | 101.5 | 100.2 | 100.2 | 101.33 | 100.31 |
| $H_3PO_3$ | 3.23 | 3.27 | 3.42 | 3.44 | — | — |
| $BPO_4$ | — | — | — | — | 4.50 | 4.50 |
| Reservoir Charge (g): | | | | | | |
| EDA | 218.3 | 219.2 | 138.2 | 138.4 | 149.26 | 149.28 |
| MEA | 0 | 0 | 10.2 | 10.2 | 10.46 | 10.49 |
| DRYING AGENT I | 199.1 | 0 | 199.9 | 0 | 182.18 | 0 |
| Heating Time to 300° C.[1] | 68 | 67 | 67 | 67 | 81 | 83 |
| Lineout Time[1,2] | 33 | 10 | 9 | 22 | 0 | 0 |
| Maximum Temperature during Lineout (°C.) | 310 | 314 | 304 | 302 | 305 | 304 |
| Maximum Pressure during Lineout (psi) | 540 | 530 | 490 | 480 | 498 | 508 |
| Temperature after Lineout (°C.) | 300 | 300 | 300 | 300 | 300 | 300 |
| Time of Reaction (including Lineout)[1] | 120 | 120 | 120 | 120 | 112 | 116 |
| Pressure when Quenched (psi) | 420 | 470 | 390 | 460 | 410 | 453 |
| Cooling Time to 200° C.[1] | 1 | 3 | 1 | 2 | 1 | 1 |

[1] All times in minutes.
[2] Time for temperature to stabilize after first reaching 300° C.

In Examples 11 and 12, the drying reservoir was charged before the reaction with dry EDA, with (Example 11) or without (Example 12) DRYING AGENT I. The data in Table 3 below indicates that the MEA conversion rate was higher in the example undergoing water removal during the reaction. An appreciable fraction of the MEA passed into the drying reservoir during the reaction, so that the drying reservoir at the conclusion of each example contained about 5% MEA. To balance this effect, Examples 13 through 16 were conducted with the drying reservoir initially charged with a 7% solution of MEA in EDA. This concentration was approximately equal to the 6.5 through 7.9% concentrations found in the drying reservoirs at the conclusion of these reactions, such that there was essentially no net outflow of MEA from the reactor during the course of the experiments. In this manner, the amount of MEA outside of the reactor at the start and end of the experiment was approximately equal thereby enabling the calculation of MEA conversion within the reactor.

TABLE 4
ANALYSIS OF COMPARATIVE WATER REMOVAL EXPERIMENTS

| Example | 11 | | 12 | | 13 | | 14 | | 15 | | 16 | |
|---|---|---|---|---|---|---|---|---|---|---|---|---|
| Product Analysis[1] | Reactor | Reservoir | Reactor | Reservoir | Reactor | Reservoir | Reactor | Reservoir | Reactor | Reservoir | Reactor | Reservoir |
| EDA | 53.9 | 78.6 | 58.4 | 77.1 | 51.9 | 79.2 | 54.0 | 80.4 | 59.6 | 81.0 | 58.9 | 78.2 |
| MEA | 6.2 | 5.1 | 8.2 | 5.4 | 7.9 | 6.5 | 12.8 | 7.9 | 11.2 | 8.4 | 15.0 | 9.2 |
| PIP | 1.19 | 1.09 | 0.92 | 0.84 | 1.10 | 1.15 | 0.98 | 0.78 | 0.77 | 0.64 | 0.70 | 0.59 |
| DETA | 19.1 | 5.4 | 14.7 | 3.2 | 21.2 | 6.6 | 17.7 | 3.5 | 16.6 | 6.5 | 14.7 | 5.0 |
| AEP | 0.86 | 0.17 | 0.62 | 0.10 | 0.95 | 0.19 | 0.80 | 0.10 | 1.2 | 0.29 | 1.0 | 0.2 |
| AEEA | 0.29 | ND | 1.6 | 0.21 | 0.67 | 0.08 | 1.20 | 0.08 | 0.87 | 0.17 | 1.3 | 0.3 |
| L-TETA | 5.61 | ND | 3.63 | ND | 6.2 | ND | 4.2 | ND | 4.0 | ND | 3.3 | ND |
| TETA | 7.4 | ND | 4.85 | ND | 8.4 | ND | 5.9 | ND | 5.8 | ND | 4.8 | ND |
| TEPA | 5.2 | ND | 2.1 | ND | 5.4 | ND | 2.1 | ND | 1.1 | ND | 1.4 | ND |
| $H_2O$[2] | 2.8 | 2.1 | 3.3 | 5.4 | 1.2 | 3.1 | 3.4 | 7.3 | 1.6 | 0.60 | 2.6 | 5.7 |
| Overall Mass Balance (%) | 99 | | 96.6 | | 98.6 | | 96.4 | | 99.5 | | 96.5 | |
| MEA Conversion, Overall (%) | 72.2 | | 65.5 | | 72.3 | | 57.4 | | 59.2 | | 48.1 | |
| MEA Conversion, Reactor only (%) | — | | — | | 80.3 | | 64.6 | | 66.1 | | 54.3 | |
| Water formed[3] (g) | 22.7 | | 19.3 | | 23.2 | | 19.0 | | 23.2 | | 15.4 | |
| Water adsorbed by drying agent (g) | 10.4 | | — | | 16.1 | | — | | 15.4 | | — | |

[1] Weight percent of isolated produced by gas chromatography; ND = not detected
[2] Weight percent of water by Karl-Fisher analysis. Reactor and Reservoir analyses shown separately.
[3] Calculated difference between hydroxy equivalents charged (based on $H_2O$ + MEA) and isolated (based on $H_2O$, MEA, AEEA).

The results show an increase in MEA consumption in the examples with water removal as compared with the examples where water is retained. Examples 15 and 16, conducted on the same basis as Examples 13 and 14 but using BPO₄ catalyst in place of the H₃PO₃ catalyst, show a similar comparative advantage for the water removal process.

The results of these Examples are even more significant then considering the fact that not all of the water was removed during the reaction as shown by the values in Table 3. Instead it was observed that a warm zone moved gradually downstream through the drying reservoir during the experiment, and disappeared about an hour before the reaction as quenched. The warmth was attributed to the heat of adsorption of water in the molecular sieve, with the observed disappearance of the zone suggesting that not enough sieve was present in the reservoir to completely adsorb the water generated by the reaction. It is believed that a larger sieve charge or other more complete means of water removal would result in even greater increased MEA conversion rates.

I claim:

1. A process for producing predominantly linearly extended polyalkylene polyamines comprising:
   (a) contacting (i) an alkylenediamine with; (ii) a difunctional hydroxy alkylene compound selected from the group consisting of alkylene glycols and alkanolamines; (iii) in the presence of a catalytically effective amount of 760 catalyst which is a phosphorus acid or acid derivative compound;
   (b) removing water during the reaction; and
   (c) recovering the polyalkylene polyamines.

2. The process of claim 1 wherein the alkylenediamine has the structure:

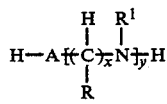

wherein A is

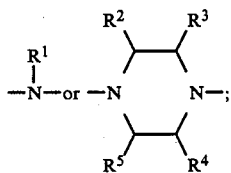

x is an integer greater than 1; y is an integer from 0 to about 6; wherein when y is 0, A is

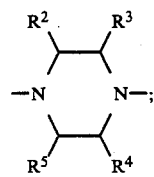

and each R, R¹, R², R³, R⁴ and R⁵ is a hydrogen or lower alkyl.

3. The process of claim 1 wherein the difunctional hydroxy alkylene compound has the structure:

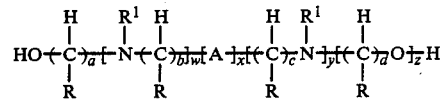

wherein A is

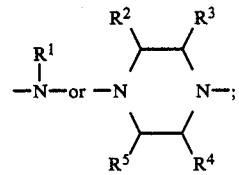

each R, R¹, R², R³, R⁴, and R⁵ is hydrogen or lower alkyl; each a, b and c is any integer greater than 1; d is 0 or an integer greater than 1; each x and z is 0 or 1; each w and y is any integer from 0 to about 6; provided that d, w and y are 0 and z is 1 when x is and z is 0 when x is 1 and d is 0.

4. The process of claim 1 wherein the water is removed continuously during the reaction.

5. The process of claim 1 wherein the water is removed by drawing off a gaseous phase of water and reaction mixture by distillation.

6. The process of claim 5 wherein the water is separated from the reaction mixture to produce a relatively anhydrous reaction mixture which is recycled to the reaction.

7. The process of claim 6 wherein the water is separated from the reaction mixture by fractional or azeotropic distillation, or adsorption.

8. The process of claim 1 wherein the reaction is conducted at temperatures of from above about 250° to about 350° C., at a pressure sufficient to provide a reaction mixture in a liquid phase, for a time period sufficient to provide a total reaction conversion of from about 10% to about 80%.

9. The process of claim 8 wherein said pressure is from about 200 to 2500 psig, and said time period is from 10 minutes to 20 hours.

10. The process of claim 1 wherein the relative proportion of alkylenediamine to difunctional hydroxy alkylene compound in mole equivalents is from about 6:1 to about 1:1 respectively.

11. The process of claim 10 wherein the relative proportion of alkylenediamine to difunctional hydroxy alkylene compound is from about 3:1 to 1:1 respectively.

12. The process of claim 2 wherein the alkylenediamine has a structure wherein x is from 2 to about 6; y is from 0 to about 2; and all R groups are hydrogen.

13. The process of claim 12 wherein the alkylenediamine is ethylenediamine or piperazine.

14. The process of claim 3 wherein the difunctional hydroxy alkylene compound has a structure wherein a is from 2 to about 6; w is from 0 to about 2; y is 0; and all R groups are hydrogen.

15. The process of claims 13 or 14 wherein the difunctional hydroxy alkylene compound is ethylene glycol, monoethanolamine or diethanolamine.

16. The process of claim 1 wherein the phosphorus acid or acid derivative compound has the structure:

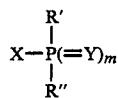

wherein Y is an oxygen or sulfur atom; m is 0 or 1; X is hydroxy, alkoxy, aryloxy, or the thioanalogs of the foregoing, alkyl or aryl substituted amino, halo, or the salts or phosphorus anhydrides or thioanhydrides of the foregoing when X is hydroxy or mercapto; R' and R" are hydrogen, alkyl, aryl or one of the groups previously defined by X.

17. The process of claim 16 wherein the phosphorus acid or acid derivative compound is phosphoric acid, phosphorous acid, boron phosphate, ferric phosphate, aluminum phosphate, hexaethylphosphorous triamide or hexamethylphosphorous triamide.

18. A process for producing predominantly linearly extended polyalkylene polyamines by reacting an alkylenediamine with a difunctional hydroxy alkylene compound selected from the group consisting of alkylene glycols and alkanolamines in the presence of a catalytically effective amount of catalyst which is a phosphorus acid or acid derivative compound wherein the improvement comprises removing water during the reaction.

19. A process for producing predominantly linearly extended polyethylene polyamines by reacting ethylenediamine with at least one of ethylene glycol, monoethanolamine and diethanolamine in the presence of a catalytically effective amount of at least one of phosphoric acid, phosphorous acid, boron phosphate, ferric phosphate, aluminum phosphate, hexaethylphosphorous triamide and hexamethylphosphorous triamide, while removing water to increase reaction conversion rates to said linearly extended polyethylene polyamines.

* * * * *